United States Patent [19]

Eicken et al.

[11] 4,420,324
[45] Dec. 13, 1983

[54] 5-AMINO-1-DI-OR TRI-SUBSTITUTED PHENYLPYRAZOLE-4-CARBOXYLIC ACID METHYL ESTERS

[75] Inventors: Karl Eicken, Wachenheim; Peter Plath, Ludwigshafen; Bruno Wuerzer, Otterstadt, all of Fed. Rep. of Germany

[73] Assignee: BASF Aktiengesellschaft, Del.X

[21] Appl. No.: 322,673

[22] Filed: Nov. 18, 1981

[30] Foreign Application Priority Data

Dec. 5, 1980 [DE] Fed. Rep. of Germany ....... 3045903
Jul. 4, 1981 [DE] Fed. Rep. of Germany ....... 3126479

[51] Int. Cl.³ ............................................. A01N 43/56
[52] U.S. Cl. ........................................ 71/92; 548/362
[58] Field of Search ............................ 548/362; 71/92

[56] References Cited

U.S. PATENT DOCUMENTS 3,515,715 6/1970 Straley et al. ...................... 548/362
3,567,735 3/1971 Druey et al. ........................ 548/362

FOREIGN PATENT DOCUMENTS 34945 9/1981 European Pat. Off. .

OTHER PUBLICATIONS

Ram et al., Arch. Pharm. (Weinheim) 1979, vol. 312, pp. 703–707.

*Primary Examiner*—Henry R. Jiles
*Assistant Examiner*—Natalia Harkaway
*Attorney, Agent, or Firm*—Keil & Witherspoon

[57] ABSTRACT

5-Amino-1-phenylpyrazole-4-carboxylic acid esters of the formula

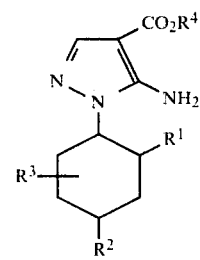

where $R^1$ is methyl, trifluoromethyl, chlorine or bromine, $R^2$ is chlorine, bromine, iodine or akylsulfonyl, $R^3$ is hydrogen, chlorine or bromine, or is methoxy in the 5-position, in which case $R^1$ and $R^2$ are chlorine, whilst $R^2$ is hydrogen if $R^3$ is chlorine in the 3-position, and $R^4$ is methyl, and herbicides containing these compounds.

4 Claims, No Drawings

5-AMINO-1-DI-OR TRI-SUBSTITUTED PHENYLPYRAZOLE-4-CARBOXYLIC ACID METHYL ESTERS

The present invention relates to 5-amino-1-phenylpyrazole-4-carboxylic acid esters, processes for the preparation of these compounds, herbicides which contain these compounds, and processes for controlling undesirable plant growth with these compounds.

5-Amino-1-phenylpyrazole-4-carboxylic acid esters which contain a chlorine atom in the phenyl radical have been disclosed in the literature (U.S. Pat. No. 3,567,735; Arch. Pharm. 312 (1979), 703). They are used as intermediates, for example for the synthesis of diuretics or antibacterial compounds. Nothing has been disclosed concerning the herbicidal properties of these compounds.

We have found that 5-amino-1-phenylpyrazole-4-carboxylic acid esters of the formula I

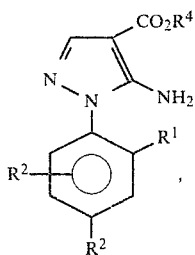

where $R^1$ is methyl, trifluoromethyl, chlorine or bromine, $R^2$ is chlorine, bromine, iodine or $C_1$-$C_3$-alkylsulfonyl, $R^3$ is hydrogen, chlorine or bromine, or is methoxy in the 5-position, in which case $R^1$ and $R^2$ are chlorine, whilst $R^2$ is hydrogen if $R^3$ is chlorine in the 3-position, and $R^4$ is alkyl of 1 to 3 carbon atoms, have a surprisingly powerful and at the same time selective herbicidal action.

The 5-amino-1-phenylpyrazole-4-carboxylic acid esters of the formula I are obtained, for example, by reacting a substituted phenylhydrazine of the formula II

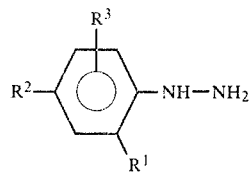

with a substituted 2-cyanoacrylic acid ester of the formula III

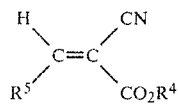

where $R^5$ is alkoxy of 1 to 4 carbon atoms, N,N-dialkylamino, where alkyl is of 1 to 4 carbon atoms, or hydroxyl, at below 70° C. to give a substituted 2'-phenylhydrazino-2-cyanoacrylic acid ester of the formula IV

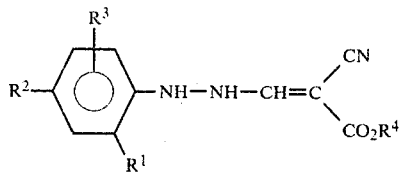

(first step), and cyclizing this intermediate in a second step by heating at above 70° C. (process A) or by treating with aqueous mineral acid at from 0° to 150° C., preferably from 20° C. to 100° C. (process B).

Suitable solvents for process A are, in particular, alcohols, e.g. methanol and ethanol, but ethers, such as dioxane, tetrahydrofuran and anisole, or hydrocarbons, such as toluene and xylene, may also be used. When the reaction in the first or second step has ended, the solution is cooled and the product formed is isolated by filtration, and if necessary purified by recrystallization. If the cyclization is carried out by process B with aqueous mineral acid, preferably with from 5 to 38% strength (% by weight) hydrochloric acid or from 5 to 50% strength sulfuric acid, the reaction mixture is diluted with from two to twenty times the volume of water when the reaction has ended, and the cyclized product is filtered off with suction, washed neutral, with the addition of dilute alkali or ammonia, and if necessary recrystallized.

5-Amino-1-phenylpyrazole-4-carboxylic acid esters of the formula I are also obtained by reacting a substituted phenylhydrazine of the formula II with a substituted 2-cyanoacrylic acid ester of the formula III in one step at above 70° C. (process C). Suitable solvents are those used in process A, preferably alcohols with boiling points above 70° C. The end products are isolated in the manner described for process A. Not less than the molar amount, and preferably the stoichiometric amount, based on the substituted phenylhydrazine of the formula II, of the 2-cyanoacrylic acid ester of the formula III is used. If instead of the free phenylhydrazines of the formula II their mineral acid salts, e.g. hydrochlorides or sulfates, are used in process A or C, the substituted phenylhydrazine of the formula II is advantageously first liberated by adding an equivalent amount of an alkali metal alcoholate or sodium acetate, and the reaction is then carried out.

Those phenylhydrazines of the formula II which are not already known can be prepared in a conventional manner (Houben Weyl, Methoden der Organ. Chemie, Volume 10/2, page 180 et seq.). The 2-cyanoacrylic acid esters of the formula III which are used are known (German Laid-Open Application DOS 2,635,841; and Chem. Ber. 97 (1964), 3397).

The 2'-phenylhydrazino-2-cyanoacrylic acid esters of the formula IV isolated when carrying out process A likewise have herbicidal properties. The Examples which follow illustrate the preparation of the intermediates and of the end products.

In the Examples, parts by weight bear the same relation to parts by volume as that of the kilogram to the liter.

Preparation of 2'-phenylhydrazino-2-cyanoacrylic acid esters of the formula IV:

EXAMPLE A 148.1 parts by weight of 2,4,6-trichlorophenylhydrazine are introduced into a solution of 108.5 parts by weight of methyl ethoxymethylene-2-cyanoacetate in 1,000 parts by volume of methanol. A crystal slurry precipitates out of the solution; the mixture is stirred for 3 hours and the crystals are filtered off with suction and dried under reduced pressure at 40° C. to give 187.4 parts by weight of methyl 2'-(2,4,6-trichlorophenyl)-hydrazino-2-cyanoacrylate of melting point 174°–175° C.

$C_{11}H_8Cl_3N_3O_2$ (M 320.5). Calculated: C 41.22, H 2.52, N 13.11. Found: C 40.9, H, 2.8, N 12.8.

EXAMPLE B

A suspension of 21.4 parts by weight of 2,4-dichlorophenylhydrazine hydrochloride in 150 parts by volume of methanol is neutralized by adding about 18 parts by weight of 30% strength sodium ethylate solution, 15.5 parts by weight of methyl ethoxymethylene-2-cyanoacetate are added and the mixture is stirred at 25° C. for 3 hours and refluxed for 15 minutes. After evaporating off the methanol from the filtrate under reduced pressure and recrystallizing the residue from ethanol (at 50° C.), 17.5 parts by weight of methyl 2'-(2,4-dichlorophenyl)-hydrazino-2-cyanoacrylate of melting point 154°–156° C. are isolated.

$C_{11}H_9Cl_2N_3O_2$ (M 286). Calculated: C 46.18, H 3.17, N 14.69. Found: C 46.0, H 3.2, N 14.8.

The following 2'-phenylhydrazino-2-cyanoacrylates of the formula IV can be prepared in a corresponding manner:

| $R^1$ | $R^2$ | $R^3$ | $R^4$ | Melting point: (°C.) |
|---|---|---|---|---|
| Cl | Cl | H | $C_2H_5$ | 175 |
| Cl | Cl | 6-Cl | $C_2H_5$ | 166 |
| Cl | Cl | 6-Cl | $i\text{-}C_3H_7$ | 130 |
| $CH_3$ | Cl | H | $CH_3$ | 140 |
| Br | Br | 6-Br | $CH_3$ | 182 |
| Cl | Br | 5-Cl | $CH_3$ | |
| Cl | Cl | 5-Cl | $CH_3$ | 195 |
| $CH_3$ | Br | H | $CH_3$ | |
| $CH_3$ | Br | 6-Br | $CH_3$ | |
| $CH_3$ | Cl | 6-Cl | $CH_3$ | |
| Cl | Cl | 6-Br | $CH_3$ | |
| Cl | Br | 6-Br | $CH_3$ | |
| Cl | Br | 6-Cl | $CH_3$ | |
| Br | Cl | 6-Br | $CH_3$ | |
| Br | Br | H | $CH_3$ | |
| Cl | Cl | 5-$CH_3O$ | $CH_3$ | |

EXAMPLE 1 (Process B)

90.0 parts by weight of methyl 2'-(2,4,6-trichlorophenyl)-hydrazino-2-cyanoacrylate are stirred in 300 parts by volume of 18% strength hydrochloric acid at 80° C. for 5 hours. After the mixture has been cooled and diluted with 500 parts by volume of water, it is filtered with suction and 70.6 parts by weight of methyl 5-amino-1-(2,4,6-trichlorophenyl)-pyrazole-4-carboxylate of melting point 179°–180° C. (active ingredient No. 1) are isolated by washing the residue neutral with water and sodium bicarbonate solution.

$C_{11}H_8Cl_3N_3O_2$ (M 320.5). Calculated: C 41.22, H 2.52, N 13.11. Found: C 41.4, H 2.8, N 12.6.

EXAMPLE 2 (Process B)

15.0 parts by weight of methyl 2'-(2,4-dichlorophenyl)-hydrazino-2-cyanoacrylate are stirred in 50 parts by volume of concentrated hydrochloric acid at 25° C. for 12 hours, and the mixture is then stirred into 500 parts by volume of ice-water. The precipitate obtained is filtered off with suction and washed neutral with water and sodium bicarbonate solution, to give 14.2 parts by weight of methyl 5-amino-1-(2,4-dichlorophenyl)-pyrazole-4-carboxylate of melting point 143°–145° C. (active ingredient No. 2).

$C_{11}H_9Cl_2N_3O_2$ (M 286). Calculated: C 46.18, H 3.17, N 14.69. Found: C 46.2, H 3.2, N 14.7.

EXAMPLE 3 (Process A)

45.0 parts by weight of methyl 2'-(2,4-dichlorophenyl)-hydrazino-2-cyanoacrylate are refluxed in 200 parts by volume of n-propanol for 6 hours. After the mixture has been cooled, 34.6 parts by weight of methyl 5-amino-1-(2,4-dichlorophenyl)-pyrazole-4-carboxylate of melting point 144°–145° C. (active ingredient No. 2) are isolated by filtration with suction.

EXAMPLE 4 (Process C)

21.2 parts by weight of 2,4,6-trichlorophenylhydrazine and 15.5 parts by weight of methyl ethoxymethylene-2-cyanoacetate are refluxed in 120 parts by volume of n-butanol for 2 hours. After the mixture has been cooled, 22.8 parts by weight of methyl 5-amino-1-(2,4,6-trichlorophenyl)-pyrazole-4-carboxylate of melting point 180°–181° C. (active ingredient No. 1) are isolated by filtration with suction.

| No. | $R^1$ | $R^2$ | $R^3$ | $R^4$ | m.p. (°C.) |
|---|---|---|---|---|---|
| 3 | Cl | Cl | H | $C_2H_5$ | 109 |
| 4 | Cl | Cl | 6-Cl | $C_2H_5$ | 105 |
| 5 | Cl | Cl | 6-Cl | $i\text{-}C_3H_7$ | 152 |
| 6 | $CH_3$ | Cl | H | $CH_3$ | 109 |
| 7 | Br | Br | 6-Br | $CH_3$ | 194 |
| 8 | Cl | Br | 5-Cl | $CH_3$ | 173 |
| 9 | Cl | Cl | 5-Cl | $CH_3$ | 175 |
| 10 | $CH_3$ | Br | H | $CH_3$ | 123 |
| 11 | $CH_3$ | Br | 6-Br | $CH_3$ | 175 |
| 12 | $CH_3$ | Cl | 6-Cl | $CH_3$ | |
| 13 | Cl | Cl | 6-Br | $CH_3$ | 199 |
| 14 | Cl | Br | 6-Br | $CH_3$ | 208 |
| 15 | Cl | Br | 6-Cl | $CH_3$ | |
| 16 | Br | Cl | 6-Br | $CH_3$ | 172 |
| 17 | Br | Br | H | $CH_3$ | |
| 18 | Cl | Cl | 5-$CH_3O$ | $CH_3$ | 182 |
| 19 | Cl | Br | 6-Cl | $CH_3$ | |
| 20 | Cl | I | H | $CH_3$ | 180 |
| 21 | Cl | H | 3-Cl | $CH_3$ | 164 |
| 22 | Cl | Cl | 6-Cl | $n\text{-}C_3H_7$ | |
| 23 | $CF_3$ | Cl | H | $CH_3$ | 146 |
| 24 | Cl | $-SO_2CH_3$ | H | $CH_3$ | 215 |

Application as herbicides may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

The herbicides contain for instance from 5 to 95, and especially from 10 to 80, wt% of active ingredient.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

EXAMPLE a 90 parts by weight of compound 1 is mixed with 10 parts by weight of N-methyl-α-pyrrolidone. A mixture is obtained which is suitable for application in the form of very fine drops.

EXAMPLE b 10 parts by weight of compound 1 is dissolved in a mixture consisting of 90 parts by weight of xylene, 6 parts by weight of the adduct of 8 to 10 moles of ethylene oxide with 1 mole of oleic acid-N-monoethanolamide, 2 parts by weight of the calcium salt of dodecylbenzenesulfonic acid, and 2 parts by weight of the adduct of 40 moles of ethylene oxide with 1 mole of castor oil.

EXAMPLE c 20 parts by weight of compound 1 is dissolved in a mixture consisting of 60 parts by weight of cyclohexanone, 30 parts by weight of isobutanol, 5 parts by weight of the adduct of 7 moles of ethylene oxide with 1 mole of isooctylphenol, and 5 parts by weight of the adduct of 40 moles of ethylene oxide with 1 mole of castor oil.

EXAMPLE d 20 parts by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil.

EXAMPLE e 80 parts by weight of compound 1 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill.

EXAMPLE f 5 parts by weight of compound 1 is intimately mixed with 95 parts by weight of particulate kaolin. A dust is obtained containing 5% by weight of the active ingredient.

EXAMPLE g 30 parts by weight of compound 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE h 40 parts by weight of compound 1 is intimately mixed with 10 parts of the sodium salt of a phenolsulfonic acid-urea-formaldehyde condensate, 2 parts of silica gel and 48 parts of water to give a stable, aqueous dispersion. Dilution in 100,000 parts by weight of water gives an aqueous dispersion containing 0.04 wt% of active ingredient.

EXAMPLE i 20 parts of compound 1 is intimately mixed with 12 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The influence of various representatives of the novel 5-amino-1-phenylpyrazole-4-carboxylates on the growth of unwanted and crop plants is demonstrated in greenhouse experiments.

The vessels employed were plastic flowerpots having a volume of 300 cm³, and which were filled with a sandy loam containing about 1.5% humus. The seeds of the test plants were sown shallow, and separately, according to species.

In the preemergence treatment, the active ingredients were immediately applied to the surface of the soil as a suspension or emulsion in water by spraying through finely distributing nozzles. The amount of active ingredient applied in this treatment was equivalent to 3.0 kg/ha.

After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 10 cm, depending on growth form, before being treated. For this treatment, either plants which had been sown directly in the pots and grown there were selected, or plants which had been grown separately as seedlings and transplanted to the experiment vessels a few days before treatment. In the case of rice, which was used in the postemergence method, peat was added to the substrate. The same applies for catchweed. In this postemergence treatment, 0.5 kg/ha of novel compounds nos. 1, 2, 6 and 7 was applied. The application rate for compared no. 8 was 1.0 kg/ha. The compound methyl 5-amino-1-(4-chlorophenylpyrazole)-4-carboxylate (A), which, although known, has hitherto not been described as a herbicide, was used as a comparative agent in the postemergence treatment at a rate of 2.0 kg/ha.

Representatives of the 2'-phenylhydrazino-2-cyanoacrylates employed for the manufacture of the 5-amino-1-phenylpyrazole-4-carboxylates (Example A, Example B) and which have herbicidal properties were applied both pre- and postemergence at a rate of 3.0 kg/ha.

Generally, no cover was placed on the vessels. The pots were set up in the greenhouse—species from warmer areas at from 20° to 35° C., and species from moderate climates at 15° to 25° C. The experiments were run for from 2 to 3 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The results show that compounds nos. 1, 2, 3, 4, 6 and 7 have, on preemergence application at a rate of 3 kg/ha, a considerable herbicidal action.

The greenhouse experiments also reveal that the active ingredients according to Examples A and B (at 3.0 kg/ha) have a good herbicidal action on pre- and postemergence application.

In these greenhouse experiments, compounds nos.1, 2, 6 and 7 have, at 0.5 kg/ha, a very good and broad action on numerous broadleaved unwanted plants. Cereal species such as winter wheat are substantially spared, or only damaged temporarily to a slight extent.

A further result of these experiments was that compound no. 8, applied postemergence at 1.0 kg/ha, has a good herbicidal action on some broadleaved weeds and is tolerated by some crop plants with only slight damage, if at all.

Prior art compound A used for comparison purposes had, applied postemergence at 2.0 kg/ha, no significant herbicidal action.

When compound no. 13 is applied postemergence at 0.5 kg/ha, it has a very good herbicidal action on broadleaved weeds, without damaging cereal species. In the same experiments, compound no. 16, at 1.0 kg/ha, also combated broadleaved weeds, with only slight and temporary damage to cereals.

If the crop plants (on leaf treatment) tolerate the active ingredients less well, application techniques may be used in which the agents are sprayed from suitable equipment in such a manner that the leaves of sensitive crop plants are if possible not touched, and the agents reach the soil or the unwanted plants growing beneath the crop plants (post-directed, lay-by treatment).

In view of the many application methods possible, the herbicides according to the invention may be used in a further, large range of crops for removing unwanted plants. Application rates may vary from 0.1 to 15 kg/ha and more.

The following crop plants may be mentioned by way of example:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rape |
| *Brassica napus* var. *napobrassica* | |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxiua* | grapefruits |
| *Citrus reticulata* | mandarins |
| *Citrus sinensis* | orange trees |
| *Coffea arabica* (*Coffea canephora, Coffea liberica*) | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum Gossypium herbaceum Gossypium vitifolium*) | cotton |
| *Helianthus annuus* | sunflowers |
| *Helianthus tuberosus* | |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nitothiana tabacum* (*N. rustica*) | tobacco |
| *Olea europaea* | olive trees |
| *Oryza sativa* | rice |
| *Panicum miliaceum* | |
| *Phaseolus lunatus* | limabeans |
| *Phaseolus mungo* | mungbeans |
| *Phaseolus vulgaris* | snapbeans, green beans, dry beans |
| *Pennisetum glaucum* | |
| *Petroselinum crispum* spp. *tuberosum* | parsley |
| *Picea abies* | Norway spruce |
| *Abies alba* | fir trees |

-continued

| Botanical name | Common name |
| --- | --- |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the novel 5-amino-1-phenyl-pyrazole-4-carboxylates may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc. A number of active ingredients which, when combined with the new compounds, give mixtures useful for widely varying applications are given below by way of example:

5-amino-4-chloro-2-phenyl-3(2H)-pyridazinone
5-amino-4-bromo-2-phenyl-3(2H)-pyridazinone
5-amino-4-chloro-2-cyclohexyl-3(2H)-pyridazinone
5-amino-4-bromo-2-cyclohexyl-3(2H)-pyridazinone 5-methylamino-4-chloro-2-(3-trifluoromethylphenyl)-3(2H)-pyridazinone
5-methylamino-4-chloro-2-(3-α,α,β,β-tetrafluoroethoxyphenyl)-3(2H)-pyridazinone
5-dimethylamino-4-chloro-2-phenyl-3(2H)-pyridazinone
4,5-dimethoxy-2-phenyl-3(2H)-pyridazinone
4,5-dimethoxy-2-cyclohexyl-3(2H)-pyridazinone
4,5-dimethoxy-2-(3-trifluoromethylphenyl)-3(2H)-pyridazinone
5-methoxy-4-chloro-2-(3-trifluoromethylphenyl)-3(2H)-pyridazinone
5-amino-4-bromo-2(3-methylphenyl)-3(2H)-pyridazinone 3-(1-methylethyl)-1H-2,1,3-benzothiadiazin-4(3H)-one-2,2-dioxide and salts
3-(1-methylethyl)-8-chloro-1H-2,1,3-benzothiadiazin-4(3H)-one-2,2-dioxide and salts
3-(1-methylethyl)-8-fluoro-1H-2,1,3-benzothiadiazin-4(3H)-one-2,2-dioxide and salts
3-(1-methylethyl)-8-methyl-1H-2,1,3-benzothiadiazin-4(3H)-one-2,2-dioxide and salts
1-methoxymethyl-3-(1-methylethyl)-2,1,3-benzothiadiazin-4(3H)-one-2,2-dioxide
1-methoxymethyl-8-chloro-3-(1-methylethyl)-2,1,3-benzothiadiazin-4(3H)-one-2,2-dioxide
1-methoxymethyl-8-fluoro-3-(1-methylethyl)-2,1,3-benzothiadiazin-4(3H)-one-2,2-dioxide
1-cyano-8-chloro-3-(1-methylethyl)-2,1,3-benzothiadiazin-4(3H)-one-2,2-dioxide
1-cyano-8-fluoro-3-(1-methylethyl)-2,1,3-benzothiadiazin-4(3H)-one-2,2-dioxide
1-cyano-8-methyl-3-(1-methylethyl)-2,1,3-benzothiadiazin-4(3H)-one-2,2-dioxide
1-cyano-3-(1-methylethyl)-2,1,3-benzothiadiazin-4(3H)-one-2,2-dioxide
1-azidomethyl-3-(1-methylethyl)-2,1,3-benzothiadiazin-4(3H)-one-2,2-dioxide
3-(1-methylethyl)-1H-pyridino-[3,2-e]-2,1,3-thiadiazin-(4)-one-2,2-dioxide N-(1-ethylpropyl)-2,6-dinitro-3,4-dimethylaniline
N-(1-methylethyl)-N-ethyl-2,6-dinitro-4-trifluoromethylaniline
N-n-propyl-N-β-chloroethyl-2,6-dinitro-4-trifluoromethylaniline
N-n-propyl-N-cyclopropylmethyl-2,6-dinitro-4-trifluoromethylaniline
N-bis-(n-propyl)-2,6-dinitro-3-amino-4-trifluoromethylaniline
N-bis-(n-propyl)-2,6-dinitro-4-methylaniline
N-bis-(n-propyl)-2,6-dinitro-4-methylsulfonylaniline
N-bis-(n-propyl)-2,6-dinitro-4-aminosulfonylaniline
bis-(β-chloroethyl)-2,6-dinitro-4-methylaniline
N-ethyl-N-(2-methylallyl)-2,6-dinitro-4-trifluoromethylaniline
3,4-dichlorobenzyl N-methylcarbamate 2,6-di-tert.butyl-4-methylphenyl N-methylcarbamate
isopropyl N-phenylcarbamate
3-methoxyprop-2-yl N-3-fluorophenylcarbamate
isopropyl N-3-chlorophenylcarbamate
but-1-yn-3-yl N-3-chlorophenylcarbamate
4-chlorobut-2-yn-1-yl N-3-chlorophenylcarbamate
methyl N-3,4-dichlorophenylcarbamate
methyl N-(4-aminobenzenesulfonyl)-carbamate
O-(N-phenylcarbamoyl)-propanone oxime
N-ethyl-2-(phenylcarbamoyl)-oxypropionic acid amide
3'-N-isopropylcarbamoyloxypropionanilide ethyl-N-(3-(N'-phenylcarbamoyloxy)-phenyl)-carbamate
methyl-N-(3-(N'-methyl-N'-phenylcarbamoyloxy)-phenyl)-carbamate
isopropyl-N-(3-(N'-ethyl-N'-phenylcarbamoyloxy)-phenyl)-carbamate
methyl-N-(3-(N'-3-methylphenylcarbamoyloxy)-phenyl)-carbamate
methyl-N-(3-(N'-4-fluorophenylcarbamoyloxy)-phenyl)-carbamate
methyl-N-(3-(N'-3-chloro-4-fluorophenylcarbamoyloxy)-phenyl)-carbamate
methyl-N-dichlorofluoromethylsulfenyl-(3-(N'-dichlorofluoromethylsulfenyl-N'-phenylcarbamoyloxy)-phenyl)-carbamate
methyl-N-dichlorofluoromethylsulfenyl-(3-(N'-dichlorofluoromethylsulfenyl-N'-3-methylphenylcarbamoyloxy)-phenyl)-carbamate ethyl-N-[3-N'-(3-chloro-4-fluorophenylcarbamoyloxy)-phenyl]-carbamate
ethyl-N-[3-N'-(3,4-difluorophenylcarbamoyloxy)-phenyl]-carbamate
methyl-N-[3-(N'-3,4-difluorophenylcarbamoyloxy)-phenyl]-carbamate methyl N-3-(4'-fluorophenoxycarbonylamino)-phenylcarbamate
ethyl N-3-(2'-methylphenoxycarbonylamino)-phenylcarbamate
methyl N-3-(4'-fluorophenoxycarbonylamino)-phenylthiolcarbamate
methyl N-3-(2',4',5'-trimethylphenoxycarbonylamino)-phenylthiolcarbamate
methyl N-3-(phenoxycarbonylamino)-phenylthiolcarbamate p-chlorobenzyl N,N-diethylthiolcarbamate
ethyl N,N-di-n-propylthiolcarbamate
n-propyl N,N-di-n-propylthiolcarbamate 2,3-dichloroallyl N,N-diisopropylthiolcarbamate
2,3,3-trichloroallyl N,N-diisopropylthiolcarbamate
3-methyl-5-isoxazolylmethyl N,N-diisopropylthiolcarbamate
3-ethyl-5-isoxazolylmethyl N,N-diisopropylthiolcarbamate
ethyl N,N-di-sec.-butylthiolcarbamate
benzyl N,N-di-sec.-butylthiolcarbamate
ethyl N-ethyl-N-cyclohexylthiolcarbamate
ethyl N-ethyl-N-bicyclo-[2.2.1]-heptylthiolcarbamate S-(2,3-dichlorallyl)-(2,2,4-trimethylazetidino)-1-carbothiolate
S-(2,3,3-trichloroallyl)-(2,2,4-trimethylazetidine)-1-carbothiolate
S-ethylhexahydro-1-H-azepine-1-carbothiolate
S-benzyl-(3-methylhexahydro-1-H-azepine-1)-carbothiolate
S-benzyl-(2,3-dimethylhexahydro-1-H-azepine-1)-carbothiolate
S-ethyl-(3-methylhexahydro-1-H-azepine-1)-carbothiolate n-propyl N-ethyl-N-n-butylthiolcarbamate
2-chloroallyl N,N-dimethyldithiocarbamate
N-methyldithiocarbamic acid, sodium salt
trichloroacetic acid, sodium salt
α,α-dichloropropionic acid, sodium salt
α,α-dichlorobutyric acid, sodium salt
α,α-β,β-tetrafluoropropionic acid, sodium salt
α-methyl-α,β-dichloropropionic acid, sodium salt
methyl α-chloro-β-(4-chlorophenyl)-propionate
methyl α,β-dichloro-β-phenylpropionate
benzamido oxyacetic acid
2,3,5-triiodobenzoic acid (salts, esters, amides)
2,3,6-trichlorobenzoic acid (salts, esters, amides)

2,3,5,6-tetrachlorobenzoic acid (salts, esters, amides)
2-methoxy-3,6-dichlorobenzoic acid (salts, esters, amides)
2-methoxy-3,5,6-trichlorobenzoic acid (salts, esters, amides)
3-amino-2,5,6-trichlorobenzoic acid (salts, esters, amides)
O,S-dimethyltetrachlorothioterephthalate
dimethyl-2,3,5,6-tetrachloroterephthalate disodium 3,6-endoxohexahydrophthalate
4-amino-3,5,6-trichloropicolinic acid (salts)
ethyl 2-cyano-3-(N-methyl-N-phenyl)-aminoacrylate
isobutyl 2-[4-(4'-chlorophenoxy)-phenoxy]-propionate
methyl 2-[4-(2',4'-dichlorophenoxy)-phenoxy]-propionate
methyl 2-[4-(4'-trifluoromethylphenoxy)-phenoxy]-propionate
2-[4-(2'-chloro-4'-trifluorophenoxy)-phenoxy]-propionic acid, sodium salt
2-[4-(3',5'-dichloropyridyl-2-oxy)-phenoxy]-propionic acid, sodium salt ethyl 2-(N-benzoyl-3,4-dichlorophenylamino)-propionate
methyl 2-(N-benzoyl-3-chloro-4-fluorophenylamino)-propionate
isopropyl 2-(N-benzoyl-3-chloro-4-fluorophenylamino)-propionate
ethyl 4-(4'-trifluoromethylphenoxy)-pentene-2-carboxylate 2-chloro-4-ethylamino-6-isopropylamino-1,3,5-triazine
2-chloro-4-ethylamino-6-(amino-2'-propionitrile)-1,3,5-triazine
2-chloro-4-ethylamino-6-(2-methoxypropyl)-2-amino-1,3,5-triazine
2-chloro-4-ethylamino-6-butyn-1-yl-2-amino-1,3,5-triazine
2-chloro-4,6-bisethylamino-1,3,5-triazine
2-chloro-4,6-bisisopropylamino-1,3,5-triazine
2-chloro-4-isopropylamino-6-cyclopropylamino-1,3,5-triazine
2-azido-4-methylamino-6-isopropylamino-1,3,5-triazine
2-methylthio-4-ethylamino-6-isopropylamino-1,3,5-triazine
2-methylthio-4-ethylamino-6-tert.butylamino-1,3,5-triazine
2-methylthio-4,6-bisethylamino-1,3,5-triazine
2-methylthio-4,6-bisisopropylamino-1,3,5-triazine 2-methoxy-4-ethylamino-6-isopropylamino-1,3,5-triazine
2-methoxy-4,6-bisethylamino-1,3,5-triazine
2-methoxy-4,6-bisisopropylamino-1,3,5-triazine
4-amino-6-tert.butyl-3-methylthio-4,5-dihydro-1,2,4-triazin-5-one
4-amino-6-phenyl-3-methyl-4,5-dihydro-1,2,4-triazin-5-one
4-isobutylidenamino-6-tert.butyl-3-methylthio-4,5-dihydro-1,2,4-triazin-5-one
1-methyl-3-cyclohexyl-6-dimethylamino-1,3,5-triazin-2,4-dione 3-tert.butyl-5-chloro-6-methyluracil
3-tert.butyl-5-bromo-6-methyluracil
3-isopropyl-5-bromo-6-methyluracil
3-sec.butyl-5-bromo-6-methyluracil
3-(2-tetrahydropyranyl)-5-chloro-6-methyluracil
3-(2-tetrahydropyranyl)-5,6-trimethyleneuracil
3-cyclohexyl-5,6-trimethyleneuracil 2-methyl-4-(3'-trifluoromethylphenyl)-tetrahydro-1,2,4-oxadiazine-3,5-dione
2-methyl-4-(4'-fluorophenyl)-tetrahydro-1,2,4-oxadiazine-3,5-dione 3-amino-1,2,4-triazole 1-allyloxy-1-(4-bromophenyl)-2-[1',2',4'-triazolyl-(1')]-ethane (salts)
1-(4-chlorophenoxy)-3,3-dimethyl-1-(1H-1,2,3-triazol-1-yl)-butan-2-one
N,N-diallylchloroacetamide
N-isopropyl-2-chloroacetanilide
N-(but-1-yn-3-yl)-2-chloroacetanilide 2-methyl-6-ethyl-N-propargyl-2-chloroacetanilide
2-methyl-6-ethyl-N-ethoxymethyl-2-chloroacetanilide
2-methyl-6-ethyl-N-(2-methoxy-1-methylethyl)-2-chloroacetanilide
2-methyl-6-ethyl-N-isopropoxycarbonylethyl)-2-chloroacetanilide
2-methyl-6-ethyl-N-(4-methoxypyrazol-1-yl-methyl)-2-chloro-acetanilide
2-methyl-6-ethyl-N-(pyrazol-1-yl-methyl)-2-chloroacetanilide
2,6-dimethyl-N-(pyrazol-1-yl-methyl)-2-chloroacetanilide
2,6-dimethyl-N-(4-methylpyrazol-1-yl-methyl)-2-chloro-acetanilide
2,6-dimethyl-N-(1,2,4-triazol-1-yl-methyl)-2-chloroacetanilide
2,6-dimethyl-N-(3,5-dimethylpyrazol-1-yl-methyl)-2-chloroacetanilide
2,6-dimethyl-N-(1,3-dioxolan-2-yl-methyl)-2-chloroacetanilide
2,6-dimethyl-N-(2-methoxyethyl)-2-chloroacetanilide 2,6-dimethyl-N-isobutoxymethyl-2-chloroacetanilide
2,6-diethyl-N-methoxymethyl-2-chloroacetanilide
2,6-diethyl-N-n-butoxymethyl-2-chloroacetanilide
2,6-diethyl-N-ethoxycarbonylmethyl-2-chloroacetanilide
2,3,6-trimethyl-N-(pyrazol-1-yl-methyl)-2-chloroacetanilide
2,3-dimethyl-N-isopropyl-2-chloroacetanilide
2,6-diethyl-N-(propoxyethyl)-2-chloroacetanilide 2-(2-methyl-4-chlorophenoxy-N-methoxyacetamide
2-(α-naphthoxy)-N,N-diethylpropionamide
2,2-diphenyl-N,N-dimethylacetamide
N-benzyl-N-isopropyl-trimethylacetamide
α-(3,4,5-tribromopyrazol-1-yl)-N,N-dimethylpropionamide
N-(1,1-dimethylpropynyl)-3,5-dichlorobenzamide
N-1-naphthylphthalamic acid
propionic acid 3,4-dichloroanilide
cyclopropanecarboxylic acid 3,4-dichloroanilide
methacrylic acid 3,4-dichloroanilide
2-methylpentanecarboxylic acid 3,4-dichloroanilide
5-acetamido-2,4-dimethyl-trifluoromethanesulfone anilide
5-acetamido-4-methyl-trifluoromethanesulfone anilide
N-4-methyl-5-(trifluoromethyl)-sulfonylamino-phenylacetamide
2-propionylamino-4-methyl-5-chlorothiazole
O-(methylsulfonyl)-glycolic acid N-ethoxymethyl-2,6-dimethylanilide
O-(methylaminosulfonyl)-glycolic acid N-isopropylanilide
O-(isopropylaminosulfonyl)-glycolic acid N-but-1-yn-3-yl-anilide
O-(methylaminosulfonyl)-glycolic acid hexamethyleneamide
2,6-dichlorothiobenzamide
2,6-dichlorobenzonitrile 3,5-dibromo-4-hydroxybenzonitrile (salts)
3,5-diiodo-4-hydroxybenzonitrile (salts)
3,5-dibromo-4-hydroxy-O-2,4-dinitrophenylbenzaldoxime (salts)
3,5-dibromo-4-hydroxy-O-2-cyano-4-nitrophenylbenzaldoxime (salts)
pentachlorophenol, sodium salt
2,4-dichlorophenyl-4'-nitrophenyl ether
2,4,6-trichlorophenyl-4'-nitrophenyl ether
2-fluoro-4,6-dichlorophenyl-4'-nitrophenyl ether
2-chloro-4-trifluoromethylphenyl-4'-nitrophenyl ether
2,4'-dinitro-4-trifluoromethyl-diphenyl ether
2,4-dichlorophenyl-3'-methoxy-4'-nitro-phenyl ether
2-chloro-4-trifluoromethylphenyl-3'-ethoxy-4'-nitrophenyl ether
2-chloro-4-trifluoromethylphenyl-3'-carboxy-4'-nitrophenyl ether (salts)
2-chloro-4-trifluoromethylphenyl-3'-ethoxycarbonyl-4'-nitrophenyl ether
2-chloro-4-trifluoromethylphenyl-3'-(2-fluoroethoxy)-4'-nitrophenyl ether
2-chloro-4-trifluoromethylphenyl-3'-ethoxycarbonylmethylthio-4'-nitrophenyl ether
2-chloro-4-trifluoromethyl-3'-methoxycarbonyl-4'-nitrophenyl ether
2,4,6-trichlorophenyl-3'-ethoxycarbonyl-methylthio-4'-nitrophenyl ether
2,4-dichlorophenyl-3'-methoxycarbonyl-4'-nitro-phenyl ether
2,4-dichlorophenyl-3'-carboxy-4-nitrophenyl ether
2-(3,4-dichlorophenyl)-4-methyl-1,2,4-oxadiazolidine-3,5-dione
2-(3-tert.butylcarbamoyloxyphenyl)-4-methyl-1,2,4-oxadiazolidine-3,5-dione
2-(3-isopropylcarbamoyloxyphenyl)-4-methyl-1,2,4-oxadiazolidine-3,5-dione
2-phenyl-3,1-benzoxazinone-(4)
(4-bromophenyl)-3,4,5,9,10-pentaazatetracyclo-[5,4,1,0$^{2,6}$0,$^{8,11}$]-dodeca-3,9-diene
2-ethoxy-2,3-dihydro-3,3-dimethyl-5-benzofuranylmethane sulfonate
2-ethoxy-2,3-dihydro-3,3-dimethyl-5-benzofuranyl-dimethylaminosulfonate
2-ethoxy-2,3-dihydro-3,3-dimethyl-5-benzofuranyl-(N-methyl-N-acetyl)-aminosulfonate
3,4-dichloro-1,2-benzisothiazole
N-4-chlorophenyl-allylsuccinimide
2-methyl-4,6-dinitrophenol (salts, esters)
2-sec.butyl-4,6-dinitrophenol (salts, esters)
2-sec.butyl-4,6-dinitrophenol acetate
2-tert.butyl-4,6-dinitrophenol acetate
2-tert.-butyl-4,6-dinitrophenol (salts)
2-tert.butyl-5-methyl-4,6-dinitrophenol (salts)
2-tert.butyl-5-methyl-4,6-dinitrophenol acetate 2-sec.amyl-4,6-dinitrophenol (salts, esters)
1-(α,α-dimethylbenzyl)-3-(4-methylphenyl)-urea
1-phenyl-3-(2-methylcyclohexyl)-urea
1-phenyl-1-benzoyl-3,3-dimethylurea
1-(4-chlorophenyl)-1-benzoyl-3,3-dimethylurea
1-(4-chlorophenyl)-3,3-dimethylurea
1-(4-chlorophenyl)-3-methyl-3-but-1-yn-3-yl-urea
1-(3,4-dichlorophenyl)-3,3-dimethylurea
1-(3,4-dichlorophenyl)-1-benzoyl-3,3-dimethylurea
1-(3,4-dichlorophenyl)-3-methyl-3-n.butylurea
1-(4-isopropylphenyl)-3,3-dimethylurea
1-(3-trifluoromethylphenyl)-3,3-dimethylurea 1-(α,α,β,β-tetrafluoroethoxyphenyl)-3,3-dimethylurea 1-(3-tert.butylcarbamoyloxyphenyl)-3,3-dimethylurea
1-(3-chloro-4-methylphenyl)-3,3-dimethylurea
1-(3-chloro-4-methoxyphenyl)-3,3-dimethylurea
1-(3,5-dichloro-4-methoxyphenyl)-3,3-dimethylurea
1-[4-(4'-chlorophenoxy)-phenyl]-3,3-dimethylurea
1-[4-(4'-methoxyphenoxy)-phenyl]-3,3-dimethylurea
1-cyclooctyl-3,3-dimethylurea
1-(hexahydro-4,7-methanoindan-5-yl)-3,3-dimethylurea
1-[1- or 2-(3a,4,5,7,7a-hexahydro)-4,7-methanoindanyl]-3,3-dimethylurea
1-(4-fluorophenyl)-3-carboxymethoxy-3-methylurea
1-phenyl-3-methyl-3-methoxyurea
1-(4-chlorophenyl)-3-methyl-3-methoxyurea
1-(4-bromophenyl)-3-methyl-3-methoxyurea
1-(3,4-dichlorophenyl)-3-methyl-3-methoxyurea
1-(3-chloro-4-bromophenyl)-3-methyl-3-methoxyurea
1-(3-chloro-4-isopropylphenyl)-3-methyl-3-methoxyurea
1-(3-chloro-4-methoxyphenyl)-3-methyl-3-methoxyurea
1-(3-tert.butylphenyl)-3-methyl-3-methoxyurea
1-(2-benzthiazolyl)-1,3-dimethylurea
1-(2-benzthiazolyl)-3-methylurea
1-(5-trifluoromethyl-1,3,4-thiadiazolyl)-1,3-dimethylurea
1-(4-benzyloxyphenyl)-3-methyl-3-methoxyurea
imidazolidin-2-one-1-carboxylic acid isobutylamide
1,2-dimethyl-3,5-diphenylpyrazolium-methylsulfate
1,2,4-trimethyl-3,5-diphenylpyrazolium-methylsulfate
1,2-dimethyl-4-bromo-3,5-diphenylpyrazolium-methylsulfate
1,3-dimethyl-4-(3,4-dichlorobenzoyl)-5-(4-methylphenylsulfonyloxy)-pyrazole
1-acetyl-3-anilino-4-methoxycarbonyl-5-methylpyrazole
3-anilino-4-methoxycarbonyl-5-methylpyrazole
3-tert-butylamino-4-methoxycarbonyl-5-methylpyrazole
2,3,5-trichloropyridinol-(4)

1-methyl-3-phenyl-5-(3'-trifluoromethylphenyl)-pyridone-(4)
1-methyl-4-phenylpyridinium chloride
1,1-dimethylpyridinium chloride
3-phenyl-4-hydroxy-6-chloropyridazine
1,1'-dimethyl-4,4'-dipyridylium-di(methylsulfate)
1,1'-di-(3,5-dimethylmorpholine-carbonylmethyl)-4,4'-dipyridylium dichloride
1,1'-ethylene-2,2'-dipyridylium dibromide
3-[1-(N-ethoxyamino)-propylidene]-6-ethyl-3,4-dihydro-2H-pyran-2,4-dione
3-[1-(N-allyloxyamino)-propylidene]-6-ethyl-3,4-dihydro-2H-pyran-2,4-dione
2-[1-(N-allyloxyamino)-propylidene]-5,5-dimethylcyclohexane-1,3-dione (salts)
2-[1-(N-allyloxyamino-butylidene]-5,5-dimethylcyclohexane-1,3-dione (salts)
2-[1-(N-allyloxyamino-butylidene]-5,5-dimethyl-4-methoxycarbonyl-cyclohexane-1,3-dione (salts)
2-chlorophenoxyacetic acid (salts, esters, amides)
4-chlorophenoxyacetic acid (salts, esters, amides)
2,4-dichlorophenoxyacetic acid (salts, esters, amides)
2,4,5-trichlorophenoxyacetic acid (salts, esters, amides)
2-methyl-4-chlorophenoxyacetic acid (salts, esters, amides)
3,5,6-trichloro-2-pyridinyl-oxyacetic acid (salts, esters, amides)

methyl α-naphthoxyacetate
ethyl 2-[4-(5'-bromopyridyl-2-oxy)-phenoxy]-propionate
ethyl 2-[4-(5'-iodopyridyl-2-oxy)-phenoxy]-propionate
n-butyl 2-[4-(5'-iodopyridyl-2-oxy)-phenoxy]-propionate
2-(2-methylphenoxy)-propionic acid (salts, esters, amides)
2-(4-chlorophenoxy)-propionic acid (salts, esters, amides)
2-(2,4-dichlorophenoxy)-propionic acid (salts, esters, amides)
2-(2,4,5-trichlorophenoxy)-propionic acid (salts, esters, amides)
2-(2-methyl-4-chlorophenoxy)-propionic acid (salts, esters, amides)
methyl 2-[4-(4'-chlorophenoxymethyl)-phenoxy]-propionate
4-(2,4-dichlorophenoxy)-butyric acid (salts, esters, amides)
4-(2-methyl-4-chlorophenoxy)-butyric acid (salts, esters, amides)
cyclohexyl-3-(2,4-dichlorophenoxy)-acrylate
9-hydroxyfluorenecarboxylic acid-(9) (salts, esters)
2,3,6-trichlorophenylacetic acid (salts, esters)
4-chloro-2-oxobenzothiazolin-3-yl-acetic acid (salts, esters)
gibelleric acid (salts)
disodium methylarsonate
monosodium salt of methylarsonic acid
N-phosphonomethyl-glycine (salts)
N,N-bis-(phosphonomethyl)-glycine (salts)
2-chloroethyl 2-chloroethanephosphonate
ammonium-ethyl-carbamoyl-phosphonate
di-n-butyl-1-n-butylamino-cyclohexyl-phosphonate
trithiobutylphosphite
O,O-diisopropyl-5-(2-benzosulfonylaminoethyl)-phosphorodithioate
2,3-dihydro-5,6-dimethyl-1,4-dithiin-1,1,4,4-tetraoxide
5-tert.-butyl-3-(2,4-dichloro-5-isopropoxyphenyl)-1,3,4-oxadiazolone-(2)
4,5-dichloro-2-trifluoromethylbenzimidazole (salts)
1,2,3,6-tetrahydropyridazine-3,6-dione (salts)
succinic acid mono-N-dimethylhydrazide (salts)
(2-chloroethyl)-trimethylammonium chloride
(2-methyl-4-phenylsulfonyl)-trifluoromethanesulfone anilide
1,1-dimethyl-4,6-diisopropyl-5-indanyl ethyl ketone
2-[1-(2,5-dimethylphenyl)-ethylsulfonyl]-pyridine-N-oxide
2-(3'-trifluoromethylphenyl)-4H-3,1-benzoxazin-4-one
2-(2-thienyl)-4H-3,1-benzoxazin-4-one sodium chlorate
ammonium thiocyanate
calcium cyanamide 2-chloro-4-trifluoromethyl-3'-ethoxycarbonyl-4'-nitrophenyl ether 1-(4-benzyloxyphenyl)-3-methyl-3-methoxyurea
2-[1-(2,5-dimethylphenyl)-ethylsulfonyl]-pyridine-N-oxide
1-acetyl-3-anilino-4-methoxycarbonyl-5-methylpyrazole 3-anilino-4-methoxycarbonyl-5-methylpyrazole
3-tert.butylamino-4-methoxycarbonyl-5-methyl-pyrazole
N-benzyl-N-isopropyl-trimethylacetamide
methyl 2-[4-(4'-chlorophenoxymethyl)-phenoxy]-propionate
ethyl 2-[4-(5'-bromopyridyl-2-oxy)-phenoxy]-propionate
ethyl 2-[4-(5'-iodopyridyl-2-oxy)-phenoxy]-propionate
n-butyl 2-[4-(5'-iodopyridyl-2-oxy)-phenoxy]-propionate
2-chloro-4-trifluoromethylphenyl-3'-(2-fluoroethoxy)-4'-nitrophenyl ether
2-chloro-4-trifluoromethylphenyl-3-(ethoxycarbonyl)-methylthio-4-nitrophenyl ether
2,4,6-trichlorophenyl-3(ethoxycarbonyl)-methylthio-4-nitrophenyl ether
2-[1-(N-ethoxamino)-butylidene]-5-(2-ethylthiopropyl)-3-hydroxy-cyclohex-2-en-1-one (salts)
2-[1-(N-ethoxamino)-butylidene]-5-(2-phenylthiopropyl)-3-hydroxy-cyclohex-2-en-1-one (salts)
ethyl 4-[4-(4'-trifluoromethyl)-phenoxy]-pentene-2-carboxylate
2-chloro-4-trifluoromethyl-3'-methoxycarbonyl-4'-nitrophenyl ether
2,4-dichlorophenyl-3'-carboxy-4'-nitrophenyl ether (salts)
4,5-dimethoxy-2-(3-α,α,β-trifluoro-β-bromoethoxyphenyl)-3-(2H)-pyridazinone
2,4-dichlorophenyl-3'-ethoxy-ethoxy-ethoxy-4'-nitrophenyl ether
2,3-dihydro-3,3-dimethyl-5-benzofuranyl-ethane sulfonate
N-[4-methoxy-6-methyl-1,3,5-triazin-2-yl-aminocarbonyl]-2-chlorobenzene sulfonamide
1-(3-chloro-4-ethoxyphenyl)-3,3-dimethylurea
ethyl 2-methyl-4-chlorophenoxy-thioacetate
2-chloro-3,5-diiodo-4-acetoxy-yiridine
1(-4-[2-(4-methylphenyl)-ethoxy]-phenyl-3-methyl-3-methoxyurea
2,6-dimethyl-N-(pyrazol-1-yl-methylenoxymethyl)-2-chloroacetanilide
2-methyl-6-ethyl-N-(pyrazol-1-yl-methylenoxymethyl)-2-chloroacetanilide
2-methyl-6-ethyl-N-(pyrazol-1-yl-ethylenoxymethyl)-2-chloroacetanilide
1-(α-2,4-dichlorophenoxypropionic acid)-3-(O-methylcarbamoyl)-anilide
1-(α-2-bromo-4-chlorophenoxypropionic acid)-3-(O-methylcarbamoyl)-anilide
methyl-N-dichlorofluoromethylsulfenyl-(3-(N'-dichlorofluoromethylsulfenyl-N'-phenylcarbamoyloxy)-phenyl)-carbamate
methyl-N-dichlorofluoromethylsulfenyl-(3-(N'-dichlorofluoromethylsulfenyl-3'-3-methylphenylcarbamoyloxy)-phenyl)-carbamate
N-(pyrazol-1-yl-methyl)-pyrazol-1-yl-acetic acid-2,6-dimethylanilide
N-(pyrazol-1-yl-methyl)-1,2,4-triazol-1-yl-acetic acid-2,6-dimethylanilide.

It may also be useful to apply the novel compounds, either alone or combined with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

TABLE 1

| List of plant names | |
|---|---|
| Botanical name | Common name |
| Abutilon theophrasti | velvet leaf |
| Avena sativa | oats |
| Brassica napus | rape seed |
| Centaurea cyanus | cornflower |
| Chenopodium album | lambsquarters |
| Datura stramonium | jimsonweed |
| Galium aparine | catchweed bedstraw |
| Gossypium hirsutum | cotton |
| Ipomoea spp. | morningglory |
| Lamium spp. | henbit |
| Malva neglecta | common mallow |
| Oryza sativa | rice |
| Sinapis alba | white mustard |
| Solanum nigrum | black nightshade |
| Triticum aestivum | wheat |
| Veronica spp. | — |

We claim:

1. A 5-amino-1-phenylpyrazole-4-carboxylic acid ester of the formula

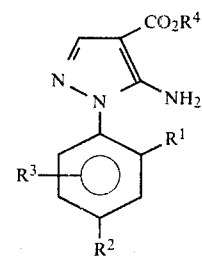

where $R^1$ is methyl, trifluoromethyl, chlorine or bromine, $R^2$ is chlorine, bromine, iodine or $C_1$–$C_3$-alkylsulfonyl, $R^3$ is hydrogen, chlorine or bromine, or is methoxy in the 5-position, in which case $R^1$ and $R^2$ are chlorine, whilst $R^2$ is hydrogen if $R^3$ is chlorine in the 3-position, and $R^4$ is methyl.

2. A 5-amino-1-phenylpyrazole-4-carboxylic acid ester selected from the group consisting of methyl 5-amino-1-(2,4,6-trichlorophenyl)-pyrazole-4-carboxylate, methyl 5-amino-1-(2,4-dichlorophenyl)-pyrazole-4-carboxylate, methyl 5-amino-1-(2-methyl-4-chlorophenyl)-pyrazole-4-carboxylate, and methyl 5-amino-1-(2,4,6-tribromophenyl)-pyrazole-4-carboxylate.

3. A herbicidal composition comprising a carrier and/or diluent and a herbicidal effective amount of a compound as defined in claim 1.

4. A method of controlling the growth of unwanted broad leafed plants which comprises: applying to the unwanted plants or to the soil which is to be freed from said plants a herbicidally effective amount of the composition defined in claim 3.

* * * * *

UNITED STATES PATENT AND TRADEMARK OFFICE
CERTIFICATE OF CORRECTION

PATENT NO. : 4,420,324
DATED : December 13, 1983
INVENTOR(S) : Karl Eicken et al.

It is certified that error appears in the above-identified patent and that said Letters Patent is hereby corrected as shown below:

IN THE ABSTRACT:

Add to the six-membered ring so that it is a conjugated system, as shown below:

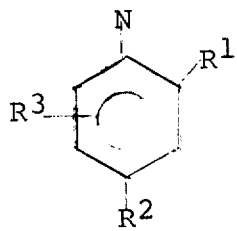

Signed and Sealed this

Seventeenth Day of April 1984

[SEAL]

Attest:

GERALD J. MOSSINGHOFF

Attesting Officer  Commissioner of Patents and Trademarks